(12) United States Patent
Baker et al.

(10) Patent No.: US 10,322,025 B2
(45) Date of Patent: Jun. 18, 2019

(54) EXTERNAL CATHETER SUPPORT DEVICE

(71) Applicants: Robert G Baker, Boynton Beach, FL (US); Allan Thornton, Cape Coral, FL (US)

(72) Inventors: Robert G Baker, Boynton Beach, FL (US); Allan Thornton, Cape Coral, FL (US)

( * ) Notice: Subject to any disclaimer, the term of this patent is extended or adjusted under 35 U.S.C. 154(b) by 0 days.

(21) Appl. No.: 15/967,917

(22) Filed: May 1, 2018

(65) Prior Publication Data

US 2018/0333291 A1    Nov. 22, 2018

Related U.S. Application Data

(60) Provisional application No. 62/602,649, filed on May 2, 2017.

(51) Int. Cl.
*A61F 5/44* (2006.01)
*A61F 5/453* (2006.01)

(52) U.S. Cl.
CPC ............ *A61F 5/4408* (2013.01); *A61F 5/453* (2013.01); *A61F 5/4405* (2013.01)

(58) Field of Classification Search
CPC ...... A61F 5/4408; A61F 5/453; A61F 5/4405; A61F 13/471; A61F 5/4401; A61F 5/40; A61F 6/04; A61F 2006/047; A61F 2006/049; A61F 5/44; A61F 5/451; Y10S 128/918
See application file for complete search history.

(56) References Cited

U.S. PATENT DOCUMENTS

| | | | | |
|---|---|---|---|---|
| 87,932 A | * | 3/1869 | Hofmann | A61F 5/453 604/349 |
| 713,900 A | * | 11/1902 | Miller et al. | A61F 5/453 604/353 |
| 1,228,452 A | * | 6/1917 | Lawrence | A61F 5/453 604/350 |
| 2,294,066 A | * | 8/1942 | Baehler | A61F 5/40 602/70 |
| 2,937,645 A | * | 5/1960 | Sachs | A61F 5/44 128/DIG. 24 |
| 4,475,909 A | * | 10/1984 | Eisenberg | A61F 5/453 600/573 |
| 4,668,229 A | * | 5/1987 | Fago | A61F 5/4401 604/327 |
| 4,994,051 A | * | 2/1991 | Walsh | A61F 5/453 604/349 |
| 5,009,649 A | * | 4/1991 | Goulter | A61F 5/453 604/349 |
| 5,036,839 A | * | 8/1991 | Weiss | A61F 5/40 602/71 |

(Continued)

*Primary Examiner* — Adam Marcetich (57) ABSTRACT

An improved external catheter support device retains a condom or external catheter on a male penis. This support device is a low cost, easy to use, and comfortable solution for incontinent men. In one embodiment, a large condom serves as a urine collection device, retained by the catheter support device. In one embodiment, absorbent materials are disposed within the condom to gelatinize released urine. In another embodiment, the support device retains an external catheter, which directs urine to a urine collection device. Various configurations of external catheter, drain tube and urine collection devices with this support device are disclosed.

14 Claims, 5 Drawing Sheets

(56) References Cited

U.S. PATENT DOCUMENTS

| | | | |
|---|---|---|---|
| 5,797,890 A | 8/1998 | Goulter | |
| 5,924,421 A * | 7/1999 | Rosbrook | A61M 25/02 |
| | | | 128/207.14 |
| 6,209,543 B1 | 4/2001 | Star | |
| 6,248,096 B1 * | 6/2001 | Dwork | A61F 5/453 |
| | | | 604/347 |
| 6,487,728 B1 * | 12/2002 | Cook | A41B 9/023 |
| | | | 2/403 |
| 6,593,509 B1 * | 7/2003 | Nitenson | A61F 13/471 |
| | | | 604/358 |
| 2008/0243097 A1 | 10/2008 | Goss | |
| 2009/0270822 A1 * | 10/2009 | Medeiros | A61F 5/451 |
| | | | 604/347 |
| 2011/0092928 A1 * | 4/2011 | Saez | A61F 5/453 |
| | | | 604/326 |
| 2012/0238976 A1 * | 9/2012 | Foster | A61F 5/4408 |
| | | | 604/353 |
| 2013/0030401 A1 * | 1/2013 | Heyman | A61F 5/453 |
| | | | 604/385.03 |
| 2014/0350501 A1 * | 11/2014 | Garcia Calero | A61F 5/453 |
| | | | 604/353 |
| 2016/0113811 A1 * | 4/2016 | Dupree | A61F 5/4408 |
| | | | 604/351 |

* cited by examiner

Items are not drawn to scale.

EXTERNAL CATHETER SUPPORT DEVICE

CROSS-REFERENCE TO RELATED APPLICATIONS

This non-provisional application is related to provisional application 62/602,649, which has a filing date of May 2, 2017 and a confirmation number of 9411.

BACKGROUND OF THE INVENTION

Field

The present disclosure generally relates to devices for addressing male urinary incontinence (UI). It does so by providing an improved support device for urine collection vessels. This support device is functionally effective and easily applied and removed without the need for ancillary tapes, adhesives, customized underwear, or harnesses suspended from the waist or belts.

Related Art

Alternative systems have deficiencies inherent in their designs or effects on the male psyche. One system requires the painstaking and precise taping of a urine-receiving tube to the end of a penis. Goss in U.S. 2008/0243097 discloses the use of custom underwear with inter-locking ring structures that require several assembly steps to engage. Goulter et al in U.S. Pat. No. 5,797,890 describes a special belt that must be worn under regular underwear to provide a support function. Absorbent pads and underwear liners are difficult to place and keep at just the right location for effective use. Absorbent pads, like diapers, are subject to leakage around the edges. Another negative aspect of diapers is that they are a tangible representation of the lack of control and virility as a man ages. This factor directly affects a man's self-esteem and self-image. Furthermore, the bulky nature of a diaper is often apparent under a man's outer garments, further increasing self-consciousness.

In U.S. Pat. No. 6,209,543, Star discloses an alternate but related solution involving a condom with an attachment means for wrapping around the scrotum. This approach employs a shaped condom that covers the entire male genital area. Its stated purpose is to provide protection against contact of bodily fluids during coitus. However, the system has at least two drawbacks that make it unsuitable for control of periodic accidental urine emissions. The first problem is that the condom enclosure exposes the glans, the penile skin and the scrotum to urine, since there is only one compartment. Secondly, there is exposure of the skin to urine and the concomitant need of extensive repeated washings if using this alternative for UI purposes. There is also the risk of irritation from extended exposure to urine, leading to skin conditions. Another problem is that enclosing the entire genital area in a waterproof device for extended periods causes discomfort through increased temperatures and sweating. Furthermore, no consideration is given for sweating underneath or enhanced pressure caused by Star's restraining strap. These characteristics prevent the use of the enhanced-protection condom for any time beyond a few minutes. Resultant discomfort would quickly cause removal by a user. Such an intercourse-related solution is unacceptable for addressing ongoing urinary incontinence.

BRIEF SUMMARY OF THE INVENTION

Urinary incontinence among males has an increasing number of sufferers as the average lifespan of modern men increases. This is augmented by the number of injured U.S. men returning from military conflicts who have suffered injuries to the pelvic region or nerves. Regardless of cause, UI effects cause embarrassment, self-consciousness, and adjustments to activities and lifestyles that many men find objectionable. Various techniques for capturing urine releases have been developed and commercialized. To achieve acceptance, solutions offered to men to cope with this condition should be simple to use and inexpensive since the condition is continually present. The present invention discloses an easy-to-use device that facilitates a low-cost solution to dealing with male urinary incontinence. In addition to low cost and simplicity, another objective of this disclosure is to require the smallest change from a UI sufferer's former lifestyle as possible. This device is designed to support urine collection vessels (i.e. condoms) and external catheters without cumbersome assemblies or customized clothing.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present disclosure. The present invention is illustrated by way of example and is not limited by the accompanying figures. Elements in the figures are illustrated for simplicity and clarity and have not necessarily been drawn to scale.

DETAILED DESCRIPTION

In the following detailed description, specific examples are described with reference to the accompanying drawings that form a part hereof. These examples describe the system and method in sufficient detail to enable those skilled in the associated arts to practice the invention. It should be understood that these are examples only, and they should not be taken as limiting. Other examples may also be practiced that are consistent with the spirit and intention of the present system and method and apparent to those skilled in the associated arts, and the scope is defined by the appended claims and their equivalents.

The present disclosure defines an improved method for avoiding embarrassing urine leaks by aging, injured or post-surgical men suffering from urinary incontinence. One or more embodiments provide a convenient system for retaining urine emissions using low cost materials. The goal of the embodiments is to provide an effective leak prevention system that is also cost effective and comfortable. This is important, as the UI problem can afflict affected men throughout the day and night. An expensive solution would be impractical and unaffordable on an ongoing basis.

One embodiment provides an improved support device that is a structurally sound method for retaining a condom or male external catheter in place on a penis. In one embodiment, the large condom acts as a flexible container to capture and hold urine. Gelatinizing material disposed within the condom reduces the mobility of any released urine. The improved support device keeps the top portion of the condom from sliding down by using a combination of bands. One band wraps around the scrotum to provide a firm attachment to the body. A second band attached to it wraps around the condom or external catheter to hold it in place on the penis. This support device is made to accommodate varying sizes of male genitalia. This allows a single production model, which maximizes manufacturing efficiencies, thereby lowering costs for eventual purchasers. An additional embodiment employs a force distribution pad that is slipped on one band to spread the support forces across a wider area than the band does by itself. Various embodiments are disclosed for housing the gelatinizing materials. A major advantage of the present disclosure is its very low cost combined with comfort. In another embodiment, an external catheter for males is applied and directs urine flow to a secondary collection device.

Another advantage of the disclosed system is that there is no requirement for custom underwear or a special belt to hold up a strap. The entire support device is embodied in a single low cost unit. The difficulty with alternative methods that use custom underwear with mating attachments is the complexity of use, discouraging user adoption. Such systems with multiple attachments are generally more expensive to produce as well.

An advantage of the present disclosure is that the majority of skin of the scrotum and penis are not enclosed within a liquid proof condom. There are only two relatively slim bands that have functional roles, so only the glans is contained with the condom or catheter. Another advantage of the present disclosure is that the bands that support and retain the condom or male external catheter are made of materials that readily breathe, allowing moisture to wick through and evaporate. This greatly improves the usability and comfort of the support device.

Another advantage of the present disclosure is that the support device is easily applied without having to remove the trousers. Clothing removal is a shortcoming in the use of adult diapers and custom underwear. In the present disclosure, removal of clothing is not required. In one embodiment, after application of the support band around and selectively the force distribution pad behind the scrotum, a retention band retains the top ring of the condom. Beside keeping the condom in place during normal activity, the retention band has the advantage of closing off the opening of the condom, preventing leaks. Further, the ease of attachment and removal is convenient and simple enough as to allow men to stand in a restroom without disrobing and slip off the condom to allow normal urination if desired and capable. Performing bodily functions as normally as possible is essential in helping a man overcome the debilitation of urinary incontinence effects post-surgery or accident.

Yet another advantage of the present disclosure is that it is undetectable under regular clothing. This is not necessarily the case with alternative bulky adult diapers or underwear with gasket and ring assemblies. The lightweight nature of the system of the present disclosure even allows active use, so men are not constrained to eliminate all of their normal activities.

Another advantage of the present disclosure is the mechanical configuration of the support band. In the normally worn position of one embodiment, the support band loops behind the scrotum to provide support. In another embodiment, a force distribution pad is easily slid onto the support band to better distribute the weight load of a condom filled with urine. Yet another advantage of this embodiment is that it prevents discomfort compared to designs that use only a thin ring around the scrotum. Furthermore, the force distribution pad behind the scrotum helps maintain the position of the connecting section between the bands at a position along the top of the penis. This location allows better urine weight load distribution and keeps the releasable attachment means on top where they are more easily seen and manipulated. If the support device were free to rotate around, the system would be more difficult to use when removing or replacing condoms.

It is another advantage of the present disclosure that the attachment means use releasable components to facilitate easy removal of the condom or external catheter. There is therefore no requirement for adhesives or tapes to retain the urine collection element, both of which attachment means are uncomfortable to remove.

A further advantage of the present disclosure is that the connecting section between the support and retention bands has an enlarged area for holding the unit while looping and attaching the bands. This area allows a firm grip between the thumb and forefinger to ease installation of the device.

Yet another advantage of this disclosure is an embodiment that places liquid-absorbing materials such as super absorbent polymers (SAP) disposed within a large condom to turn the urine into a gel. The gelling action eliminates the sloshing feel, reduces urine contact with the skin, and reduces the possibility of a leak. Most SAP gels form a viscous mass that does not flow like liquids.

The improved support device also reduces the stretching forces inherent in self-contained UI systems by distributing the support load across a larger area than just the penis. In addition, this disclosure identifies a low-cost and practical system for safely containing accidental urinary emissions. There is a need for such a device for millions of men who suffer this condition. This is facilitated by employing mass-produced receptacle bags (large condoms) and conventional external catheters as urine collection devices. Such mass-produced devices dramatically lower the cost of a whole solution.

Figure 1:
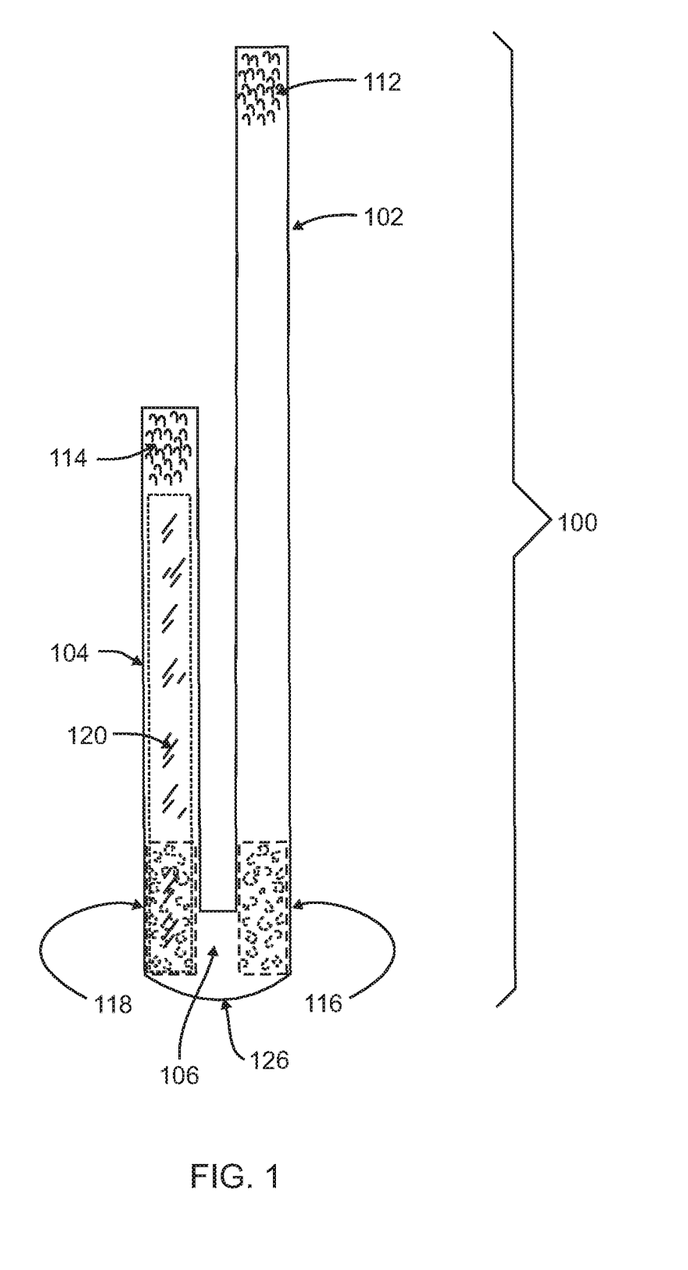
FIG. 1 is a frontal view of a first embodiment of the improved support device of the present disclosure laid flat for explanation.

Referring now to FIG. 1, the diagram shows one configuration of an embodiment of an improved condom or external catheter support device 100 when it is laid out flat. The support device 100 consists of subsections including a support band 102, a retention band 104, and a connecting section 106. The subsections 102, 104 and 106 of support device 100 are preferably made from a single piece of flexible material. The material is flexible to allow it to better conform to genital structures. The material of support device 100 is also preferably breathable to permit evaporation of moisture from genital skin. In another embodiment, the material of support device 100 is elastomeric. Support band 102 and retention band 104 may alternatively be made as separate elements that are then joined by connecting section 106 through stitching, heat-seaming, adhesives, or other joining processes. Connecting section 106 has an expanded midsection 126 to make it easier to grasp between the fingers when applying the support device 100. To perform their functions, the ends of the support band 102 and retention band 104 are configured to form closed loops around different areas of the male genitalia. Closed loops are established by using attachment means that are released and re-attached, as the support device 100 is meant for adjustability for men of differently sized male anatomies. There are many suitable materials that are useful for releasable attachment. The releasable attachment means are one or more fastener types from the collection of Velcro®, hook-and-loop materials, snaps, and adhesive strips. For explanation purposes, hook-and-loop attachment means are used to describe the operation of the device throughout this disclosure. However, hook-and-loop attachment means are listed solely as examples and are non-limiting with respect to the scope of this disclosure or its implementation. Other materials that provide holding and closure forces and that are manually released and reset are acceptable substitutes. In an alternate embodiment, one-time-use attachment means such as tape or adhesive may be employed to lower cost.

Continuing with reference to FIG. 1, support band 102 forms a closed loop and encircles the male scrotum next to the perineum and pubic bone. The support band 102 has a first fastening means disposed on a first portion 112 of the band 102 and a second fastening means disposed on a second portion 116 of the band 102. The first fastening means is configured to releasably mate with the second fastening means at various positions when the first portion 112 of the band 102 is overlapped with the second portion 116 of the band 102. For purposes of illustration and not to limit the scope of the device or its implementation, hook-and-loop material is used as an example of the fastening means. Hook material is illustrated in FIG. 1 as the example first fastening means at the first portion 112 of band 102. Loop material is illustrated in FIG. 1 as the example second fastening means at the second portion 116 of band 102. The illustrated loop material at the second portion 116 of band 102 is on the opposite side of the band 102 from the illustrated hook material at the first portion 112 of band 102. This configuration permits the first and second portion fastening means to engage when a loop is formed around the genital components. The first fastening means at first portion 112 is configured to releasably mate with the second fastening means at various positions. This occurs when the first portion 112 of the band is overlapped with the second portion 116 of the band 102. The surface area of support band 102 covered by loop material at the second portion 116 of band 102 is larger than the corresponding area of hook material at the first portion 112. This expanded area provides an adjustment capability that allows for different loop circumferences that are both effective and comfortable for different sized men.

Further with FIG. 1, the retention band 104 forms a closed loop and encircles the ringlike structure at the proximal end of an external catheter or condom applied to a penis. The retention band 104 has a first fastening means disposed on a first portion 114 of the band 104 and a second fastening means disposed on a second portion 118 of the band 104. The first fastening means at first portion 114 is configured to releasably mate with the second fastening means at various positions. This occurs when the first portion 114 of the band 104 is overlapped with the second portion 118 of the band. The retention band 104 is approximately parallel to the support band 102. For purposes of illustration only, hook-and-loop material is again used as an example of the fastening means. Hook material is illustrated in FIG. 1 as the example first fastening means at the first portion 114 of band 104. Loop material is illustrated in FIG. 1 as the example second fastening means at the second portion 118 of band 104. The illustrated loop material at the second portion 118 of band 104 is on the opposite side of the band 104 from the illustrated hook material at the first portion 114 of band 104. The first and second portion fastening means engage when a loop is formed around the penile shaft. The surface area of retention band 104 covered by loop material at the second portion 118 of band 104 is larger than the corresponding area of hook material at the first portion 114. This is done to allow for closure of the support band 104 loop at different circumferences. This adjustment capability allows for different loop circumferences that are both effective and comfortable for different sized men. A hypoallergenic nonslip coating 120 is selectively bonded to the side of the retention band 104 that faces the penile shaft. This coating improves the grip of the retention band 104 on the outer surface of the condom or external catheter. This coating can selectively be rolled, sprayed or painted on. Alternatively, it may be applied as a non-slip film or tape with an adhesive back for attachment.

In another embodiment, closure and attachment of bands 102 and 104 is performed with tape or adhesives designed for use only one time. The releasable attachment means at portions 112, 116, 114 and 118 are optionally replaced by this alternative mechanism to lower cost.

Still with reference to FIG. 1, a connecting section 106 joins the support band 102 and the retention band 104. Since band 102 and band 104 are approximately parallel, the connecting section 106 is approximately orthogonal to the parallel axes of band 102 and band 104. Connecting section 106 has an enlarged midsection 126 for grasping with fingers during application. It is an advantage of this disclosure that the enlarged midsection eases grasping with either hand. It is a further advantage of this disclosure that the attachment area is on top where it is visible to the user for convenient application.

Figure 2:
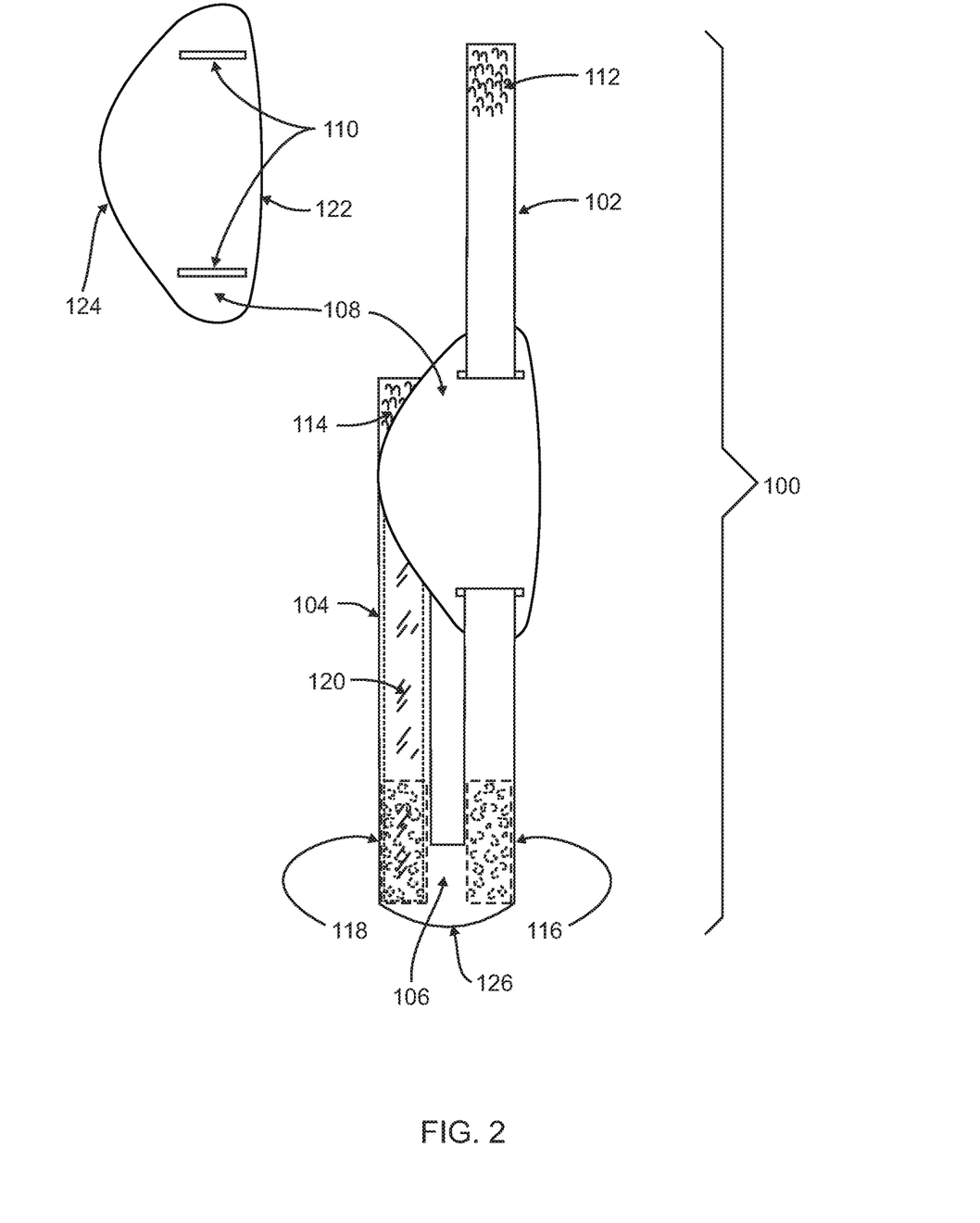
FIG. 2 is a frontal view of another embodiment of the improved support device of the present disclosure with an accessory to improve comfort.

In another embodiment shown in FIG. 2, a force distribution pad 108 is illustrated as a separate accessory and also illustrated in place on support band 102. The force distribution pad 108 has rounded edges to prevent discomfort and is removably positioned on the support band 102 prior to application. In use, the force distribution pad 108 is slid onto support band 102 through slits 110 before the loop of the support band 102 is closed around the male genitalia. A substantially straight pad side 122 is configured closer to the perineum, while the wider pad side 124 is oriented away from the body. The orientation of the pad 108 is such that support band 102 holds up the ends of the pad 108 outside of slits 110 so that the pad conforms to the loop shape.

Figure 3:
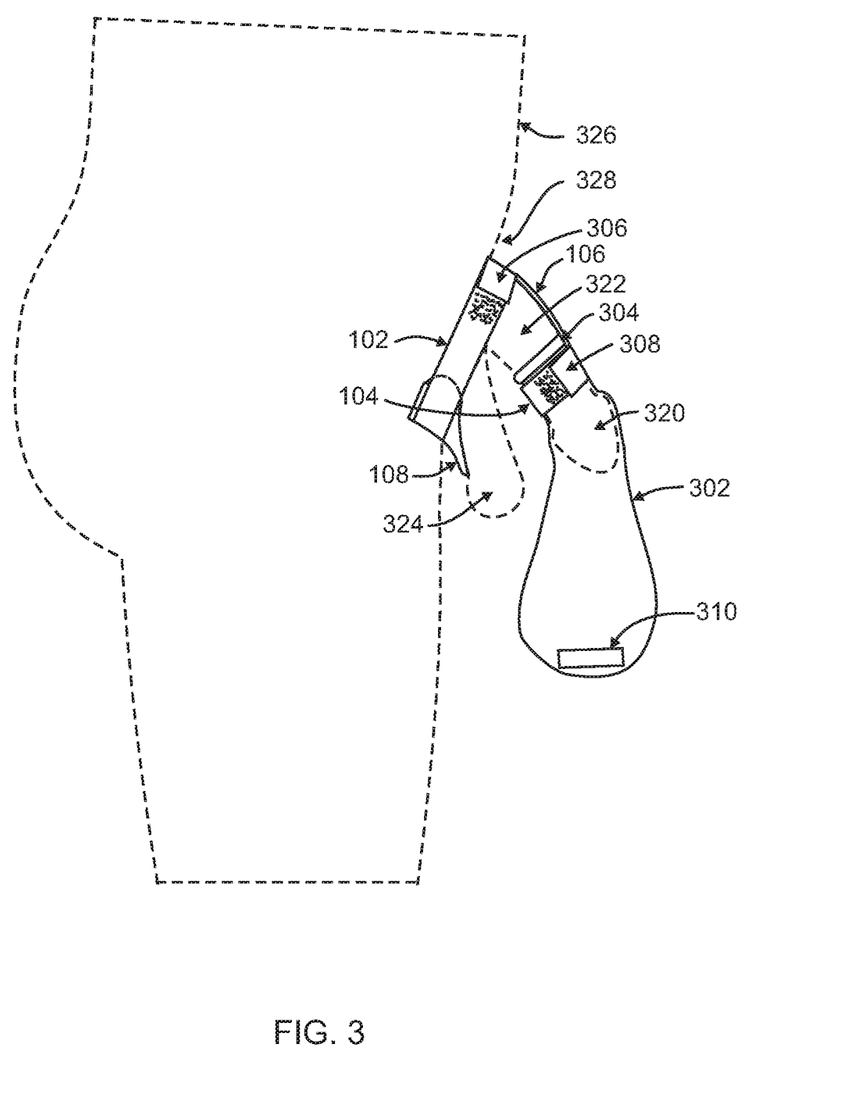
FIG. 3 is a side perspective view of an embodiment of a urinary incontinence system employing the support device of the present disclosure with a large condom and gelatinizing materials.

FIG. 3 shows a side perspective view of an embodiment of the support device 100 in place on a male user, a portion of whose body is shown in outline form 326. In this embodiment, a large condom 302 is held in position to create an improved male urinary incontinence system. In this embodiment, the support band 102 is wrapped over the penis 322 and behind the scrotum 324. The support band 102 encircles the scrotum 324 next to the perineum (not separately identified in this view) and the pubic bone 328. FIG. 3 also illustrates the use and position of force distribution pad 108. Region 306 is where the first fastening means disposed on a first portion 112 of the band 102 overlaps a second fastening means disposed on a second portion 116 of the band 102. The first fastening means is configured to releasably mate with the second fastening means at various positions. This flexibility in mating position is for the purpose of comfort adjustments and effective attachment.

Because of the extra surface area of loop material at the second portion 116 of band 102, the support device 100 accommodates men of different physical sizes. The mating first and second fastening means are preferably brought together on top in region 306 where they are easily seen by the user. This aids application and later removal. The connecting section 106 of support device 100 thus rests on top of the penis 322 to better support weight loads of expelled urine in condom 302. It is an advantage of one embodiment using the force distribution pad 108 that the connecting section 106 is kept on top by light pressure applied by the force distribution pad 108 against the back of scrotum 324.

In the embodiment shown in FIG. 3, a condom 302 is used to contain accidentally released urine. The condom 302 has a ringlike structure 304 that is found at the open end of a condom. In FIG. 3, the condom 302 is shown applied to a wearer's penis 322. In use, the ringlike structure 304 is spaced at least as far away from the glans 320 as the width of retention band 104. The glans 320 and ringlike structure 304 have larger diameters than that of the penis 322 when the condom 302 has been applied. The condom 302 is held in place on a penis 322 by wrapping the retention band 104 of the support device 100 around the condom 302 distal to the ringlike structure 304. Closure of the retention band 104 occurs between the ringlike structure 304 and the glans 320. The resultant circumference is smaller than the ringlike structure 304 and the glans 320 to keep the condom 302 from slipping off the penis when the condom 302 has expelled urine in it. The first fastening means disposed on a first portion 114 of the band 102 overlaps with the second fastening means. The second fastening means is disposed on a second portion 118 of the band 104. Engagement of the two fastening means forms a releasable attachment at region 308.

Continuing with another embodiment using FIG. 3, absorbent gelling materials are disposed within the interior volume of condom 302. Such materials are added to the condom interior prior to applying the condom 302 to a penis 322. The absorbent materials are selectively contained in a package 310 as illustrated in FIG. 3 or in alternative forms. The absorbent materials are contained within the interior volume of the condom 302 in at least one of a several forms. One of these material forms is a small package that expands upon exposure to urine. Another form is a small package that dissolves upon exposure to urine. Yet another form is absorbent material bonded to a sheet or shreds thereof, or enclosed in a capsule. See FIG. 4 for various alternative packaging embodiments. Either a package 310 or alternative packaging methods is carried to the bottom of the condom 302 by gravity. The small package 310 containing absorbent materials is designed to selectively expand, break open, or dissolve as urine is introduced. Exposure to urine turns the urine into a gel that is less mobile and less likely to leak out.

Figure 4:
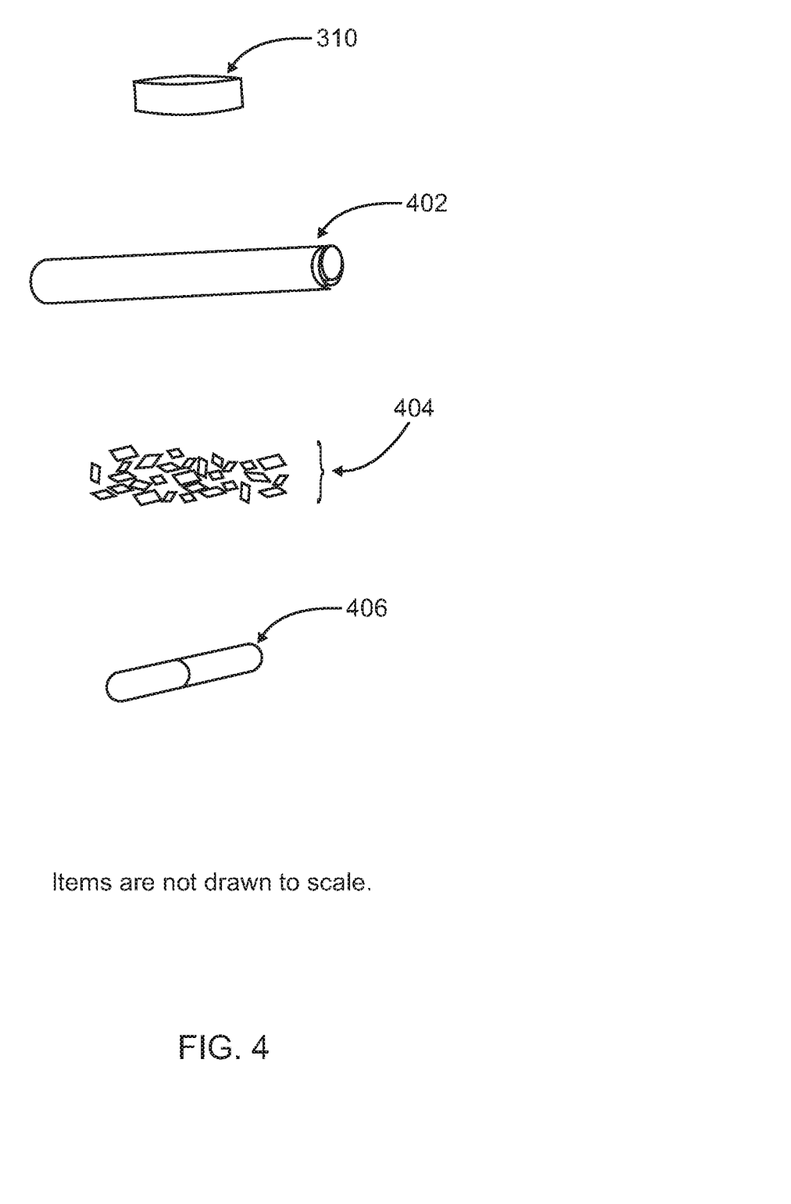
FIG. 4 shows illustrations of several embodiments of gelatinizing materials.

Gelatinizing materials used within the condom 302 are alternatively packaged in one of several different embodiments, as shown in FIG. 4. Package 310 is a liquid transmissible material that allows urine to readily flow through from outside the package to the absorbent materials. In one embodiment, the package 310 expands as the absorbent materials expand. In another embodiment, the package 310 dissolves to allow freer distribution of the absorbent materials. Yet another embodiment involves binding the absorbent materials to a sheet 402, which is optionally rolled up for insertion into the condom 302. Another embodiment is a cross-cut of an absorbent sheet 402 to yield a collection of absorbent paper shreds 404. Yet another embodiment packages the absorbent materials in a liquid-soluble capsule 406 that breaks down readily upon introduction of urine into the condom 302. In still another embodiment (not shown), the absorbent materials are disposed within the interior volume of the condom 302 as loose materials without packaging containment.

Figure 5:
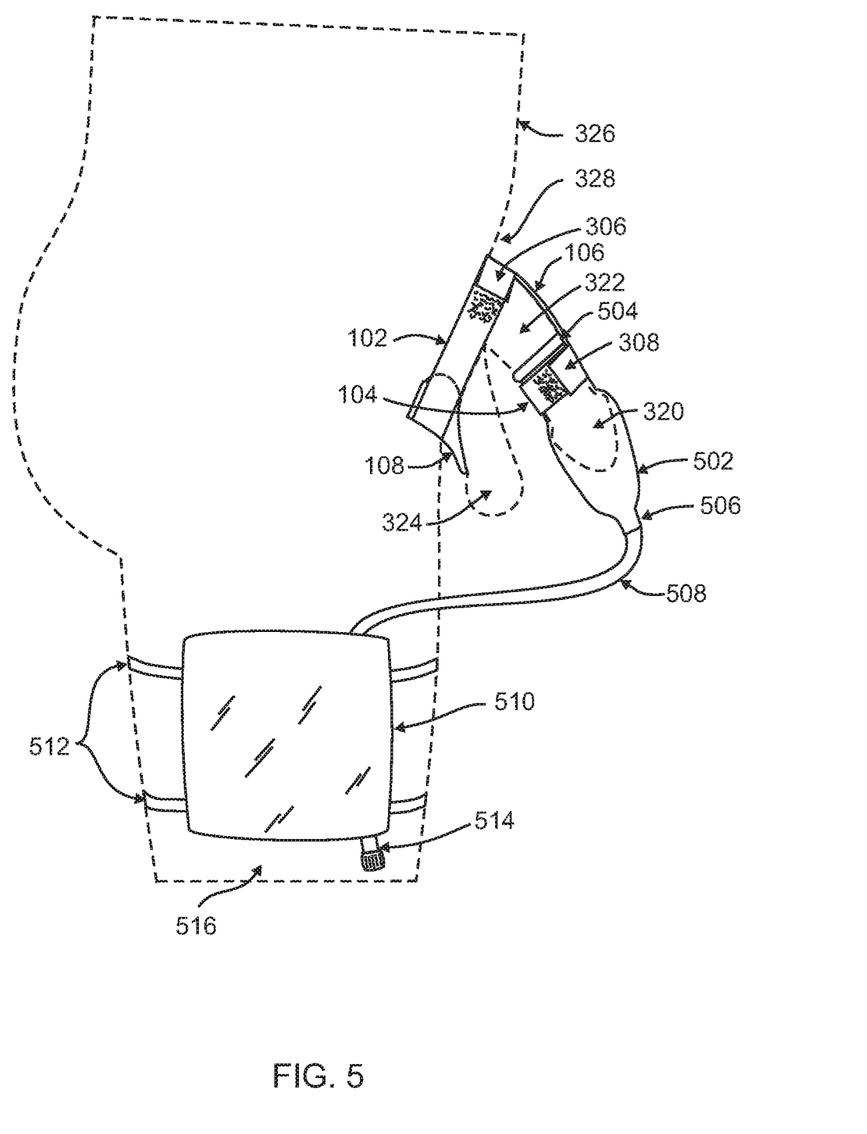
FIG. 5 is a side perspective view of an embodiment of a urinary incontinence system employing the support device of the present disclosure with an exemplar male external catheter, drain tube and leg-worn bag.

FIG. 5 shows a side perspective view of another embodiment of the support device 100 in place on a male user, a portion of whose body is shown in outline form 326. In this embodiment, a male external catheter 502 is held in position to provide another embodiment of an improved male urinary incontinence system. In this embodiment, a male external catheter 502 directs urine releases to a separate urine collection device 510. In this embodiment as with FIG. 3, the support band 102 is wrapped around the penis 322 and behind the scrotum 324. The support band 102 encircles the scrotum 324 next to the perineum (not separately identified in this view) and the pubic bone 328. FIG. 5 also illustrates the use and position of force distribution pad 108. Region 306 is where the first fastening means disposed on a first portion 112 of the band 102 overlaps a second fastening means disposed on a second portion 116 of the band 102. The first fastening means is configured to releasably mate with the second fastening means at various positions for the purpose of comfort adjustments and effective attachment. Because of the extra surface area of loop material at the second portion 116 of band 102, the support device 100 accommodates men of different physical sizes. The mating first and second fastening means are preferably brought together on top in region 306 where they are easily seen by the user. This aids application and later removal. As when using a condom to collect urine, the connecting section 106 of support device 100 rests on top of the penis 322 to better retain the male external catheter 502. In the embodiment shown in FIG. 5, the connecting section 106 is kept on top by light pressure applied by the force distribution pad 108 against the back of scrotum 324. A male external catheter ordinarily has an integrated ringlike structure at the proximal application end and a draining connection port at the distal end in relation to a man's pelvis. In this embodiment, an external catheter 502 for males is shown applied to a wearer's penis 322. The ringlike structure 504 at the proximal end of external catheter 502 is spaced at least as far away from the glans 320 as the width of retention band 104. The glans 320 and ringlike structure 504 have larger diameters than that of the penis 322 when the male external catheter 502 has been applied. Closure of the retention band 104 between the ringlike structure 504 and the glans 320 at a circumference smaller than the ringlike structure 504 and the glans 320 thus keeps the male external catheter 502 from slipping off the penis. The catheter 502 is held in place on the penis 322 by wrapping the retention band 104 of the support device 100 around the catheter distal to the ringlike structure 504. The hook material at the retention attachment end 114 overlaps with the loop material at the retention attachment area 118. This action forms a releasable attachment at region 308. The hypoallergenic nonslip coating on retention band 104 improves the grip of the retention band 104 on the outer surface of the external catheter 502.

In one embodiment shown in FIG. 5, the distal end of male external catheter 502 has a catheter draining connection port 506. This connection port 506 connects to a separate drain tube 508. In one embodiment, the drain tube 508 conveys urine to a detachable urine collection device 510. An important physical positioning requirement for the urine collection device 510 is that it is at a lower level than the male external catheter 502. The purpose of this positioning is so that gravity conveys the urine to the collection device 510. In this embodiment in FIG. 5, the collection device is shown attached to the inside of a leg 516. The obscuring leg is not shown. The urine collection device 510 is releasably attached to a man's leg using at least one of straps, bands, and tape. However, various options are available for supporting the collection device 510. Depending on size and based on user preference, this bag may positioned in one of several ways. It may selectively be carried within brief-type underwear, attached to a user's leg 516 with releasable straps 512 as illustrated, or hung at a lower elevation on a bed or chair (not shown). Only attachment to the user's leg 516 is illustrated in FIG. 5. There are several optional combinations of drain tubes and collection devices. For example, in another embodiment not shown, the drain tube 508 and collection device 510 are integrated into a single assembly. Further still, another embodiment configures the collection device 510 with a drain port 514 for emptying the bag without removing it. Still other combinations of external catheter 502, drain tube 508 and collection device 510 may readily be manufactured and implemented. Various configurations are possible that follow the spirit of the present disclosure. These descriptions and illustrations should not be considered as limitations of scope for the present disclosure.

Non-Limiting Examples

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language).

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

We claim:

1. An improved external catheter support device for retaining a condom or external catheter on a male penis, comprising:
    a flexible support band configured to encircle a male scrotum next to a perineum and pubic bone, further comprising a first fastening means disposed on a first portion of the support band and a second fastening means disposed on a second portion of the support band, wherein the first fastening means is configured to releasably mate with the second fastening means at various positions when the first portion of the support band is overlapped with the second portion of the band;
    a flexible retention band configured to encircle a ringlike structure at a proximal end of an external catheter or condom, further comprising a third fastening means disposed on a first portion of the retention band and a fourth fastening means disposed on a second portion of the retention band and where the third fastening means is configured to releasably mate with the fourth fastening means at various positions when the first portion of the retention band is overlapped with the second portion of the band, the retention band configured to be held in position approximately parallel to the support band;
    a connecting section joining the support band and the retention band and approximately orthogonal to the main axes of the parallel support band and retention band, the section configured to be aligned along the top side of a penis and with an enlarged midsection for grasping with fingers; and
    a material that is configured to flexibly conform to genital structures and breathable to permit evaporation of moisture from genital skin.

2. The support device of claim 1 wherein the material of the support device is elastomeric.

3. The support device of claim 1 wherein the fastening means is selected from a group consisting of hook and loop, snaps, adhesives, and adhesive strips.

4. The support device of claim 1 wherein a force distribution pad is removably positioned on the support band.

5. The support device of claim 1 coupled with a condom that has an integrated ringlike structure at an open end, the condom configured to be held in place on a penis by wrapping the retention band of the support device around the condom distal to the ringlike structure.

6. The support device and condom of claim 5, further comprising absorbent gelling materials disposed within a condom interior volume.

7. The absorbent materials of claim 6 wherein the absorbent materials are contained within the condom interior volume in at least one of a small package that expands upon exposure to urine, a small package that dissolves upon exposure to urine, bonded to a sheet or shreds thereof, and a capsule.

8. The absorbent materials of claim 6 wherein the absorbent materials are disposed within the condom interior volume as loose materials.

9. The support device of claim 1 coupled with a male external catheter that has an integrated ringlike structure at a proximal application end of the catheter and a draining connection port at a distal end of the catheter, the catheter configured to be held in place on a penis by wrapping the retention band of the support device around the catheter distal to the ringlike structure.

10. The support device coupled with male external catheter of claim 9, wherein a drain tube connects to the catheter draining connection port.

11. The support device coupled with male external catheter of claim 10, wherein the drain tube connects to a detachable urine collection device.

12. The support device coupled with male external catheter of claim 10, wherein the urine collection device of claim 11 is configured to releasably attach to a man's leg using at least one of straps, bands, and tape.

13. The support device coupled with male external catheter of claim 10, wherein the drain tube of claim 11 is integrated with the urine collection device of claim 11 as a single assembly.

14. The support device of claim 1 in which the fastening means comprise one time use tape or adhesive.

* * * * *